United States Patent
Allegretti et al.

[11] Patent Number: 5,908,863
[45] Date of Patent: Jun. 1, 1999

[54] GEMINAL CARBOXYLIC ACIDS AND ESTERS THEREOF PHARMACEUTICAL FORMULATIONS CONTAINING THEM USEFUL IN THE TREATMENT OF BONE DYSMETABOLISM

[75] Inventors: Marcello Allegretti; Marco Mantovanini; Gianfranco Caselli; Simonetta Fiorentino; Gaetano Clavenna; Carmelo A. Gandolfi, all of Milan, Italy

[73] Assignee: Dompe' S.p.A., L'Aquila, Italy

[21] Appl. No.: 08/806,594

[22] Filed: Feb. 26, 1997

[30] Foreign Application Priority Data

Feb. 27, 1996 [IT] Italy ................... MI96A0359

[51] Int. Cl.⁶ ................... A61K 31/225; A61K 31/35; C07C 229/24; C07D 309/12
[52] U.S. Cl. ................... 514/547; 514/227.5; 514/238.8; 514/315; 514/459; 514/561; 514/574; 544/59; 544/106; 546/248; 549/419; 549/426; 560/127; 560/171; 562/507; 562/571
[58] Field of Search ................... 514/256, 277, 514/227.5, 238.8, 315; 544/333, 335, 59, 106; 546/341, 342, 343, 248; 562/491, 507, 571; 459/547, 561, 574; 549/419, 426; 560/127, 171

[56] References Cited

FOREIGN PATENT DOCUMENTS

| | | | |
|---|---|---|---|
| 0279707 | 8/1988 | European Pat. Off. | 546/343 |
| 0087567 | 7/1981 | Japan | 546/343 |
| WO 9410127 | 5/1994 | WIPO . | |

OTHER PUBLICATIONS

CA 79:43221, 1973.

CA 57:12371h, 1962.

CA 52:18309f, 1958.

*Primary Examiner*—Yogendra N. Gupta
*Attorney, Agent, or Firm*—Griffin, Butler, Whisenhunt & Szipl, LLP

[57] ABSTRACT

Compounds of formula I:

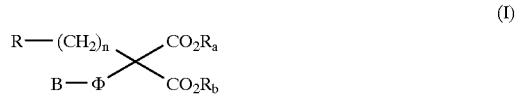

wherein $R_a$, $R_b$, $\Phi$, B and R are as defined in the disclosure, have antagonistic activity on osteoclast hyper-reactivity.

7 Claims, No Drawings

GEMINAL CARBOXYLIC ACIDS AND ESTERS THEREOF PHARMACEUTICAL FORMULATIONS CONTAINING THEM USEFUL IN THE TREATMENT OF BONE DYSMETABOLISM

SUMMARY OF THE INVENTION

The present invention relates to geminal carboxylic acids and esters thereof of formula (I):

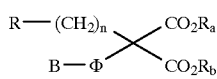
(I)

wherein:

$R_a$ and $R_b$ are independently hydrogen, an alkali or alkaline-earth metal cation, an ammonium or $C_1$–$C_{10}$ alkylammonium cation, $C_1$–$C_4$ alkyl, $C_1$–$C_{10}$ alkoxyethyl, allyl, p-methoxybenzyl, amino-$C_2$–$C_4$ alkyl;

$\Phi$ is a group of formula —(Y)q—(CH$_2$)r in which Y is CH$_2$, O or S;

B is a 2-propyl group; a tert-butyl group; a phenyl optionally mono-, di- or tri-substituted with a substituent selected from the group of hydroxy, $C_1$–$C_4$ alkoxy, $C_1$–$C_4$-alkylthio, $C_1$–$C_7$ acyloxy, chlorine, tert-butyl, trifluoromethyl, isobutyl; α-, β-, γ-pyridyl; $C_3$–$C_7$-cycloalkyl; α- or β-naphthyl; 6-hydroxy- or 6-$C_1$–$C_4$-alkoxy-β-naphthyl; m-benzoylphenyl; 3,5-dimethylisossazol-4-yl; thien-2-yl; 1,3-dithian-2-yl or 1,3-dithian-5-yl; 1,3-dioxan-5-yl; pyrimidin-2-yl; triazin-2-yl; —(CH$_2$)$_2$—(OCH$_2$—CH$_2$)$_t$H; —(CH$_2$)$_2$—(OCH$_2$—CH$_2$)$_t$—OH; a heterocycle of formula (II):

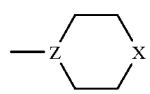
(II)

in which –Z< is a group H-C< or —(CH$_Z$)$_2$—N<, whereas X is a single bond (between 2 carbon atoms), CH$_2$, O, S, or NR$_c$ wherein R$_c$ is hydrogen, $C_1$–$C_4$-alkyl, $C_1$–$C_8$-acyl, tert-butoxycarbonyl (BOC), 9-fluorenylmethoxycarbonyl (FMOC), benzyloxycarbonyl, p-methoxybenzyloxycarbonyl, phenyl, benzyl, benzhydryl;

R is selected from the group consisting of:
β-pyridyl; fur-2-yl; 5-dimethylaminomethyl-fur-2-yl;
phenyl; phenoxy or phenylthio, being phenyl as defined above;
hydroxy, chlorine, bromine, iodine, (preferably bromine), $C_1$–$C_7$ acyloxy, $C_1$–$C_7$ sulfonate or a group of formula —S—C(=NR$_d$)—NHR$_e$ in which R$_d$ and R$_e$ are independently hydrogen, $C_1$–$C_4$-alkyl, $C_3$–$C_7$ cycloalkyl, benzyl;
4,5-dihydro-imidazol-2-yl-2-thio; 3,4,5,6-tetrahydro-pyrimidin-2-yl-2-thio;

a group of formula (III):

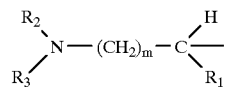
(III)

wherein:
when $R_1$ is hydrogen and $R_2$ is hydrogen, $C_1$–$C_7$-alkyl, $C_3$–$C_7$ cycloalkyl or benzyl, $R_3$ is hydrogen, $C_1$–$C_4$-alkyl, tert-butoxycarbonyl (BOC), 9-fluorenylmethoxycarbonyl (FMOC), benzyloxy, p-methoxybenzyloxycarbonyl, one of the groups of formula R$_d$N=C(YR$_e$)— or S; R$_d$NH—C(=NH), R$_d$NH—C(=N—CN); —C(=CH—NO$_2$)-NHCH$_3$, wherein R$_d$ and R$_e$ are as defined above and Y is 0 or S;
when $R_1$ is hydrogen, $R_2$ and $R_3$, taken together with the nitrogen atom which they are linked to, can form a 5- or 6- membered nitrogen heterocyclic ring of formula (IV):

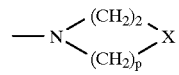
(IV)

wherein X and R$_c$ are as defined above;
when $R_2$ is hydrogen, $C_1$–$C_4$-alkyl, $R_1$ and $R_3$, taken together with the N and C atoms which they are linked to, can form a 5- to 7- membered saturated nitrogen heterocyclic ring;

m is zero or an integer 1 to 3;
n is zero or an integer 1 to 6;
p is the integer 2 or 3 but preferably the integer 2;
q is zero or the integer 1;
r is zero or an integer 1 to 3;
t is an integer 1 to 3;

the optically active forms, i.e. the enantiomers, diastereomers and the mixtures thereof and the pharmaceutically acceptable salts thereof.

The invention also relates to a process for the preparation of the compounds of formula (I) and the pharmaceutical compositions containing them for human and veterinary uses.

DESCRIPTION OF PREFERRED EMBODIMENTS

Examples of $C_1$–$C_4$ alkyl groups are: methyl, ethyl, propyl, isopropyl, butyl, isobutyl, tert-butyl, preferably methyl, ethyl, tert-butyl.

Examples of amino-$C_2$–$C_4$-alkyl are dialkylamino-$C_2$–$C_4$-alkyls wherein $C_2$–$C_4$-alkyl is ethyl, propyl, butyl and the dialkylamino residue is dimethyl, diethyl, piperidin-1-yl and preferably dimethylaminoethyl.

Examples of $C_1$–$C_4$-alkoxyethyl groups are: methoxyethyl, ethoxyethyl, propoxyethyl, isopropoxyethyl, butoxyethyl, tert-butoxyethyl; preferably ethoxyethyl.

Examples of $C_1$–$C_4$-alkoxyphenyl are $C_1$–$C_4$-alkoxyethers of phenols and polyphenols and preferably p-methoxyphenyl, p-tert-butoxyphenyl, 3,4,5-trimethoxyphenyl, 4-hydroxy-3,5-dimethoxyphenyl, 3-hydroxy-4-methoxyphenyl, 4-hydroxy-3-methoxyphenyl, preferably 3,4,5-trimethoxyphenyl.

Examples of $C_1$–$C_4$-alkylthiophenyl are p-methylthiophenyl, p-tert-butylthiophenyl and preferably p-methylthiophenyl.

Examples of $C_1$–$C_7$-acyloxy are formyl, acetyl and benzoyl.

Examples of 6-$C_1$–$C_4$-alkoxy-β-naphthyl are 6-tert-butoxy and 6-methoxy, preferably 6-methoxy-β-naphthyl.

Examples of $C_3$–$C_7$-cycloalkyl are cyclopropyl, cyclobutyl, cyclopentyl, cyclohexyl and cycloheptyl, preferably cyclohexyl or cyclopentyl.

Examples of $C_1$–$C_7$-sulfonate are methanesulfonate, benzenesulfonate, preferably p-toluenesulfonate.

Examples of $C_1$–$C_7$ alkyl groups are: methyl, ethyl, propyl, isopropyl, butyl, isobutyl, tert-butyl, n-heptyl, 3,3-dimethyl-but-2-yl, 2,2-dimethyl-pent-3-yl, preferably 3,3-dimethyl-but-2-yl.

Examples of heterocycles of formula (IV) are: pyrrolidine, piperidine, piperazine, 4-substituted-piperazines, morpholine, thiomorpholine, azepine, oxazepine, thiazepine, preferably pyrrolidine and morpholine.

Examples of preferred cations are those of lithium, sodium, potassium, magnesium, calcium, ammonium, triethylammonium, tromethamine or those of 1-amino acids such as glycine, lysine, valine, leucine, isoleucine, cysteine, methionine and arginine.

In compounds of formula (I), $C_1$–$C_4$-alkoxyphenyl is preferably methoxyphenyl, $C_1$–$C_7$-acyloxyphenyl is preferably formyloxyphenyl or acetoxyphenyl, $R_1$ is preferably hydrogen, the group —$NR_2R_3$ is preferably $NH_2$, methylamino, ethylamino, isopropylamino, dimethylamino or diethylamino; or $R_2$ and $R_3$ form a pyrrolidin-1-yl, piperidin-1-yl, morpholin-4-yl, thiomorpholin-4-yl group, or a piperazin-1-yl-4 group optionally substituted as 4-ureido, 4-methyl, 4-phenyl, 4-benzyl, 4-benzhydryl.

When the carboxylic groups of the compounds of formula (I) are undissociated or esterified, each of any basic groups present, i.e. any single —$NR_2R_3$ and amino-$C_2$–$C_4$ alkyl groups present, can be salified with non toxic, pharmaceutically acceptable acids such as acetic, trifluoroacetic, formic, propionic, fumaric, maleic, malonic, benzoic, salicylic, 3,4,5-trimethoxy-benzoic, methanesulfonic, benzenesulfonic, camphosulfonic, lactic, aspartic, glutamic, R- or S- thiazolidine-2-carboxylic acids, cysteine, N-acetyl-cysteine, carboxymethylcysteine; or inorganic acids such as phosphoric, sulfuric, hydrochloric and hydrobromic acids.

Preferred compounds of formula (I) are those wherein:

1) $R_a$ and $R_b$ are $C_1$–$C_4$ alkyl, particularly ethyl, hydrogen or a cation as defined above;

2) R is a group of formula (III) as defined above, 5-dimethylamino-fur-2-yl or β-pyridyl;

3) n is an integer 2 to 5;

4) Φ is a group of formula —$(CH_2)_{1-3}$ and B is cycloalkyl $C_3$–$C_7$, particularly cyclohexyl;

5) Φ is a oxygen atom and B is 4-tetrahydropyranyloxy;

6) Φ is a group of formula —$(CH_2)_{1-2}$—O— and B is $C_1$–$C_7$ acyloxy, particularly 2-ethoxy;

7) Φ is a sulfur atom and B is $C_3$–$C_7$ cycloalkyl, particularly cyclohexyl;

8) the combination of two or more of the substituents of the above points.

Specific examples of the compounds of the invention are:
ethyl 4-(5-dimethylaminomethyl-fur-2-ylmethyltio)-2-cyclohexylmethyl-2-ethoxycarbonyl-butanoate;
ethyl 3-(3-pyridyl)-2-cyclohexylmethyl-2-ethoxycarbonyl-propanoate;
ethyl 5-BOC-amino-2-(4-tetrahydropyranyloxy)-2-ethoxycarbonyl-pentanoate;
ethyl 5-BOC-amino-2-[2-(ethoxy)-ethyloxy]-2-ethoxycarbonyl-pentanoate;
5-BOC-amino-2[(2-ethoxy)ethyloxy]-2-carboxy-pentanoic acid and the lithium salt thereof;
5-BOC-amino-2-(4-tetrahydropyranyloxy)-2-carboxy-pentanoic acid and the lithium, tromethamine and L-lysine salts thereof;
ethyl 5-BOC-amino-2-(3-cyclohexylpropyl)-2-ethoxycarbonyl-pentanoate;
ethyl 4-(pyrrolidin-1-yl)-2-cyclohexylmethyl-2-ethoxycarboxy-butanoate;
ethyl 3-(5-dimethylaminomethyl-fur-2-yl)-2-cyclohexylmethyl-2-ethoxycarbonyl-propanoate;
ethyl 5-amino-2-(4-tetrahydropyranyloxy)-2-ethoxycarbonyl-pentanoate;
ethyl 5-amino-2-[2-(ethoxy)-ethyloxy]-2-ethoxycarbonyl-pentanoate;
ethyl 5-isopropylamino-2-cyclohexylmethyl-2-ethoxycarbonyl-pentanoate;
N-[(4,4-diethoxycarbonyl),4-tetrahydropyranyloxy]-butyl guanidinium sulfate;
N-[(4,4-diethoxycarbonyl),4-cyclohexylthio],N'-ethylcyanoguanidine;
S-[(4,4-diethoxycarbonyl),4-(2-(2-ethoxy)ethyl)]-butyl isothiouronium bromide.

The compounds of formula (I) are obtained by means of a process of substitution at the methine C-H of malonic esters of formula (V), wherein:

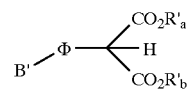

(V)

$R'_a$ and $R'_b$ can be $C_1$–$C_4$-alkyl, $C_1$–$C_4$-alkoxyalkyl, allyl, p-methoxybenzyl, Φ is as defined above and B' is hydrogen; 2-propyl; tert-butyl; phenyl optionally mono-, di- and tri-substituted with a substituent selected from the group of $C_1$–$C_4$ alkoxy, $C_1$–$C_4$-alkylthio, $C_1$–$C_7$ acyloxy, chlorine, tert-butyl, trifluoromethyl, isobutyl; α-, β-, γ-pyridyl; $C_3$–$C_7$-cycloalkyl; fur-2-yl; α-, β-naphthyl; 6-$C_1$–$C_7$-acyloxy- and 6-$C_1$–$C_4$-alkoxy-β-naphthyl; m-benzoylphenyl, 3,5-dimethylisoxazol-5-yl; thien-2-yl; 1,3-dithian-2-yl and 1,3-dithian-5-yl; 1,3-dioxan-5-yl; pyrimidin-2-yl; triazin-2-yl, —$(CH_2)_2$—$(OCH_2$—$CH_2)_t$H and —$(CH_2)_2$—$(OCH_2$—$CH_2)_t$—O—$C_1$—$C_7$ acyl, a heterocycle of formula (II), wherein, being Z selected from the group of H—C< and —$(CH_2)_2$—N<, X is a single bond (between 2 carbon atoms), $CH_2$, O, S, $NR'_c$ wherein $R'_c$ can be $C_1$–$c_4$-alkyl, $C_1$–$C_8$-acyl, tert-butoxycarbonyl (BOC), 9-fluorenylmethoxycarbonyl (FMOC), benzyloxycarbonyl, p-methoxybenzyloxycarbonyl, phenyl, benzyl, benzhydryl.

The process comprises the alkylation of a compound of formula (V) with a compound of formula (VI):

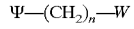

(VI)

wherein n is as defined above, and is selected from:
β-pyridyl;
phenyl, acyloxyphenyl, phenoxy or phenylthio as defined above;
hydroxy, $C_1$–$C_7$-acyloxy;

a group of formula (VII):

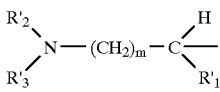

(VII)

wherein m is as defined above, and:
when $R'_1$ is hydrogen and $R'_2$ is hydrogen, $C_1$–$C_7$-alkyl, $C_3$–$C_7$-cycloalkyl or benzyl, $R'_3$ is hydrogen, $C_1$–$C_4$-alkyl, tert-butoxycarbonyl (BOC), 9-fluorenylmethoxycarbonyl (FMOC), benzyloxy or p-methoxybenzyloxycarbonyl,
when $R'_1$ is hydrogen, $R'_2$ and $R'_3$ taken together with the nitrogen atom which are linked to, can form a 5- or 6- membered nitrogen heterocyclic ring of formula (IV):

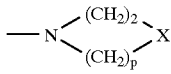

(IV)

wherein X and $R'_c$ are as defined above;
when $R'_2$ is hydrogen, $C_1$–$C_4$-alkyl, $R'_1$ and $R'_3$, taken together with the N and C carbon atoms which are linked to, can form a 5- to 7- membered saturated heterocyclic ring, as defined above;
W is chlorine, bromine, iodine or a sulfonic ester such as mesylate, p-toluenesulfonate, benzenesulfonate, trifluoromethanesulfonate;
to give a compound of formula (Ia):

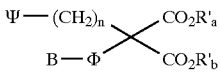

(Ia)

wherein $R'_a$, $R'_b$, Ψ, B' and Φ are as defined above, which can be optionally transformed into a compound of formula (I), for example through ester interchange reactions, cleavage of any protecting groups present, N-alkylation or acylation, O-acylation or O-substitution with thiol groups to give mercaptans and the straight or cyclic thioureids thereof, salification of free amino and/or carboxylic groups. For example, the diesters of the compounds of formula (Ia), can be hydrolyzed or transformed into the geminal dicarboxylic acids thereof to be recovered as salts or free acids or re-esterified with a suitable alcohol $R_aOH$ or $R_bOH$ or mixtures thereof. When Ψ in the compounds of formula (Ia) is the residue of a primary and/or secondary amino-protecting group, after cleavage of the protecting group itself, the resulting amine can be transformed into the corresponding ureide, thioureide, isothioureide, guanidine, cyanoguanidine and N'-alkylderivatives thereof using methods well known in preparative organic chemistry, and described recently by, for example, C. R. Rasmussen, Synthesis 460, 1988; A. B. Miller et al, ibidem, 777, 1986; C. A. Marianoff and al. J. Org. Chem., 51, 1882, 1986; Org. Synth., 21, 89, 1948; E. Schmidt et al., Ann, 6, 1, 1959; H. A. Staab, ibidem, 657, 104, 1982; Monatsh. fur Chemie, 90, 41, 1959; K. Ley, Ang. Chem., 78, 672, 1968; Helv. Chim. Acta, 1716, 1966; J. Org. Chem., 30, 2465, 1965. Analogously, when Ψ in the compounds of formula (Ia) is the residue of a primary or secondary hydroxy-protecting group or a hydroxy group, this can be converted into the corresponding sulfonic acid ester (mesylate, triflate, benzenesulfonate, p-toluenesulfonate), using well known methods, or in the corresponding alkyl halide, preferably iodide or bromide, which, by reaction with a suitable thiol, will give the compounds of formula (Ia) wherein R is a group —S—C(=NR$_d$)-NHR$_e$, 4,5-dihydroimidazol-2-yl-2-thio; 3,4,5,6-tetrahydro-pyrimidin-2-yl-2-thio, (R$_d$ and R$_e$ being as defined above).

The hydrolysis of the esters of the gemdicarboxylic acids of the compounds of formula (Ia) is effected preferably with LiOH aqueous solutions of LiOH in a $C_1$–$C_3$ alcohol, in a temperature range from room temperature to –10° C., in a time from a few hours to 48 hours. Preferred solvent is methanol and the reaction is performed in the presence of at least two molar equivalents of the base or of a slight excess thereof. The allyl esters can be removed in the presence of Pd-phosphines and of an alkanoic acid alkali salt. The transformation of a compound of formula (Ia) into a compound of formula (I) wherein $R_a$, $R_b$ are hydroxy, can be carried out, by hydrolysis of the ester groups, prior to removing all the protecting groups optionally present.

A compound of formula (I) wherein $R_a$, $R_b$ are hydroxy can be converted into another compound of formula (I) wherein $R_a$ and $R_b$ are the counter-ions thereof with a conventional salification process with a pharmaceutically acceptable inorganic or organic base. Particularly preferred organic bases are basic α-amino acids such as L-lysine, L-arginine and L-N'-methylarginine and aminoalcohols such as tromethamine and D-glucamine.

The malonic acid diesters of formula (V):

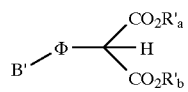

(V)

are commercially available compounds or can be prepared from commercially available products with known methods.

Thus, malonic acid esters of formula (V) wherein Φ is a S atom can be obtained by thiolating the halomalonate diesters $R'_aO_2C$—(CH—G)—$CO_2R'_b$ wherein G is Cl, Br, I, preferably Br, with a suitably reactive mercaptan, such as (B'—S⁻Na⁺) or by reacting a reactive malonate, such as $R'_aO_2C$—(CH⁻ Na⁺)—$CO_2R'_b$ with a sulfenyl halide (B'—S⁺ G$_a$⁻) being G$_a$ Cl or Br, preferably Br, and B', $R'_a$ and $R'_b$ as defined above. More precise indications about these preparation methods can be found in the following literature. Use of sulfenyl halides: Brintzinger et al., Chem. Ber., 86, 557, 1953; Mattioda et al., J. Med. Chem., 18, 553, 1975, Labushagne et al., Tetrah. Lett., 3571 (1976); use of halomalonates and thiols: in Kaloustian et al, J. Amer. Chem. Soc., 98, 956, 1976; E. Juaristi et al., J. Org. Chem., 55, 33, 1990; J. Grossert et al., J. Chem. Soc. Comm., 20, 1183, 1982; R. Aveta et al., Gazz. Chim. It., 116, 649, 1986; use of sulfanes in Labuschagne et al., J. Chem. Soc. Perk. Trans. I, 955, 1978; or thioacetimide esters halohydrates in H. Singh et al., Indian J. Chem. Sect. B, 21, 272, 1982 and 24, 131, 1985 esters; or p-toluenethiosulfonic S-esters in Hayashi et al., Chem. Pharm. Bull., 19, 1557, 1971.

Still more particularly, malonic acid diesters of formula (V) wherein Φ is an O atom are prepared by reaction of a B'—OH alcohol with a diazomalonic acid ester of formula (VIII):

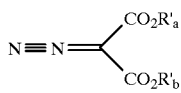

(VIII)

in the presence of dimer Rh diacetate, (B', R'$_a$ and R'$_b$ as above described). The O-alkylation technique derives from that described by Paulissen et al., Tetrah. Lett., 2223 (1973) in the case of carboxylic acid α-diazo esters. Alternatively, the reaction can also be performed in the presence of silica gel, according to the process described by Ohno et al., Tetrah. Lett., 4005 (1979) as far as carboxylic acid α-diazo esters are concerned.

Malonic acid diesters of formula (V) and methods suitable for the preparation thereof are described inter alia in WO 94/10127, PCT/EP93/02941 (23.10.1993) in the Applicant's name.

The compounds of the invention can be used in the treatment of osteoporosis and bone dysmetabolism diseases, in the treatment of malignant hypercalcemia and of Paget's disease.

The metabolic abnormalities of bone tissue are often characterized by a loss in the bone mass and they can be related both to a matrix mineralisation incapability and an inadequate matrix formation, which pathologies are also known under the names of osteomalacia and osteoporosis, respectively. Bone tissue is an active, continuously formed tissue, whose equilibrium depends on an appropriate control of the bone neo-formation and degradation processes which are regulated by the functional activity of osteoblasts and osteoclasts, which are cells respectively presiding the osteo-genic and osteolytic functionalities.

Osteoclasts are considered to be the main responsible for bone resorption. Pits following to bone resorption processes are observed, for example, when enzymatically recovered primary cultures of rabbit osteoclasts are grown on bovine devitalized bone fragments. As a consequence, medicaments that may maintain the osteoclastic activity while inhibiting any hyperactivity in all the osteoclastic hyper-reactivity pathological conditions, in which bone resorption processes prevail on the neo-formation ones, are of paramount interest.

The compounds of the invention, when tested n vitro, according to the method described by Y. Su et al., Endocrinology, 131, 1497, 1992 in a concentration scalar range from $10^{-12}$ to $10^{-6}$ M, evidence an effective inhibition of the formation of bone pits without cytotoxyc effects on the osteoclasts themselves.

Moreover, the compounds of the invention are effective in vivo, after both subcutaneous and oral administrations, in inhibiting bone resorption which is usually observed in female mice after ovariectomy. The experimental method used, with minor changes, is that described by R. Kitazava et al., (J. Clin. Inv., 94, 2397, 1994). For the final evaluation of the percent changes in the bone mass of shin bone and long bone, compared with non-treated, ovariectomized controls, the experimental method refers, with the appropriate changes, to the method described by E. I. Barengolts et al., (Calcif. Tissue Int., 52, 239, 1993).

Specific examples of the compounds of the invention are:
A) 5-BOC-amino-2-[2-(ethoxy)-ethoxy]-2-carboxy-pentanoic acid lithium salt;
B ethyl 5-BOC-amino-2-[2-(ethoxy)-ethoxyl]-2-carboxypentanoate;
C) ethyl 5-BOC-amino-2-cyclohexylmethyl-2-carboxypentanoate;
D) ethyl 5-BOC-amino-2-[4-tetrahydropyranyl-1-oxy]-2carboxy-pentanoate;
E) ethyl 5-BOC-amino-2-[3-cyclohexyl-prop-1-yl]-2-carboxypentanoate;

In a series of tests, the compounds were evaluated compared with:
ALN:alendronate;
F) ethyl 5-BOC-amino-2-[2-tetrahydropyranyl-1-oxy]-2-carboxy-pentanoate;
G) 5-BOC-amino-2-[2-tetrahydropyranyl-1-oxy]-2-carboxypentanoic acid lithium salt;
taken as positive standards. The synthesis of the compounds F and G has been performed according to the process described in WO 94/10127 PCT/EP93/02941 (23.10.1993).

After subcutaneous administration, compared with −1,83±1,53 and −3,06±1,50% decreases in bone mass in ovariectomized female mice, respectively for shin bone and long bone, in the animals treated with the compounds ALN, A, F, G, the following results were obtained:

|  | mg/kg | % changes shin bone | long bone |
|---|---|---|---|
| ALN | 20 (mg) | 0.78 ± 1.69 | 0.02 ± 1.86 |
|  | 20 (mg) | 1.+9 ± 2.46 | 0.66 ± 3.23 |
|  | 20 (mg) | 3.43 ± 0.95 | 4.04 ± 1.21 |
| F | 10 | 2.20 ± 0.85 | −0.60 ± 0.73 |
|  | 30 | 6.49 ± 0.83 | 1.56 ± 1.46 |
| G | 10 | −0.40 ± 1.00 | 1.29 ± 0.26 |
|  | 30 | 3.57 ± 2.03 | 6.12 ± 3.04 |
|  | 100 | 2.28 ± 1.75 | 2.80 ± 2.55 |
| A | 10 | 0.34 ± 1.49 | 0.84 ± 1.43 |
|  | 30 | 1.68 ± 1.80 | 2.15 ± 2.57 |

After oral administration, compared with −0,50±1,74 and −7,92±1,63 decreases in bone mass in ovariectomized female mice, respectively for shin bone and long bone, in the animals treated with the compounds ALN, B, C, D, F, the following results were obtained:

|  | mg/kg | % changes shin bone | long bone |
|---|---|---|---|
| ALN | 6 | 4.86 ± 1.30 | 0.08 ± 1.62 |
| F | 25 | −4.97 ± 3.10 | −13.42 ± 3.68 |
| B | 25 | −1.59 ± 1.51 | −3.61 ± 1.66 |
| C | 25 | 1.98 ± 1.78 | −2.90 ± 2.03 |
| D | 25 | 4.05 ± 1.44 | −1.67 ± 1.44 |

The evaluation of all the test results proves that the compounds of the present invention are particularly suitable for attaining the desired therapeutical purposes. More particularly, the compounds of the present invention turned out to be effective even after oral administration, which is obtained not so effectively as with tartronic acids and the acetal ethers thereof.

The administration of the compounds of the invention causes no adverse effects on bone growth and mineralisation.

For the envisaged therapeutical purposes, the compounds of the invention are suitably formulated in pharmaceutical compositions using conventional techniques, such as those described in "Remington's Pharmaceutical Sciences Handbook" Mack Publishing Co., New York, USA, 17th Ed., 1985.

The pharmaceutical compositions of the invention can be administered intramuscularly, intravenously, as a bolus and preferably orally, in the form of capsules, tablets, syrups and optionally as controlled-release forms. The daily dosage will vary depending on a number of factors, such as the severity of the disease and the conditions of patient (sex, weight, age): the dose will vary from 2 to 1200 mg of compound daily, optionally in repeated administrations. Higher dosages and more protracted administration times could be considered, in view of the low toxicity of the compounds of the invention.

The following examples further illustrate the invention.

EXAMPLE 1

48 g of p-tosylazide (J. Prakt. Chem., 125, 323, 1930) are added in small portions, under stirring and at room temperature, to a solution of diethyl malonate (40 g) in abs. ethanol (EtOH); when the addition is completed, stirring is continued for 5 min., then a solution of triethylamine (34 ml) in 30 ml of abs. ethanol is added dropwise keeping stirring overnight. When the reaction is complete, (TLC, $SiO_2$ Hexane/AcOEt 8:2), ethanol is evaporated off and the residue is suspended in hexane/AcOEt 7:3 to separate p-tosylamide which is filtered off. After a second precipitation with hexane/AcOEt 7:3, 40 g of good purity ethyl diazomalonate (90% yield) are obtained.

EXAMPLE 2

A catalytic amount of $[Rh(OAc)_2]_2$ is added to a solution of ethyl diazomalonate (20 g) in ethylene glycol (40 ml) which acts both as reagent and solvent. Carefully checking the reaction mixture reactivity, and under stirring, the mixture is heated gradually to a temperature of 50° C., keeping stirring at this temperature for 24 h., which is the time necessary for the starting diazoderivative to disappear (TLC, $SiO_2$ $CHCl_3$/MeOH 98:2). The solvent excess is evaporated, under reduced pressure at 40° C.; the residual alcohol is distilled off azeotropically with toluene. After purification on a silica gel column, eluent $CHCl_3$/MeOH 98:1, 18.2 g of ethyl 2-(2-ethoxyethyl)oxy-malonate are obtained (69% yield). $^1$HNMR ($CDCl_3$, ppm): 4.6 (1H, s, O=C—(CHO—)—C=O); 4.2 (4H, q, O=C—O—$CH_2$—$CH_3$); 3.75 (2H, t, O=C—(CHO—$CH_2$—)—C=O, J 5 Hz); 3.6 (2H, t, O=C—(CHO—$CH_2$—$CH_2$—)—C=O, J 5 Hz); 3.45 (2H, q, —O—$CH_2$—$CH_3$, J 4 Hz); 1.25 (6H, t, O=C—O—$CH_2$—$CH_3$, J 7 Hz); 1.1 (3H, t, —O—$CH_2$—$CH_3$, J 7 Hz).

EXAMPLE 3

A solution of 4-hydroxy-tetrahydropyrane (11.5 g) and ethyl diazomalonate (18.7 g) in 30 ml of dichloromethane, added with a catalytic amount of $[Rh(OAc)_2]_2$, is refluxed under stirring for 24 h until the starting diazoderivative completely disappears. The mixture is concentrated to small volume and the residue is eluted through silica gel, eluent $CHCl_3$/MeOH 98:1, to obtain 16.4 g of ethyl 4-tetrahydropyranyloxy-malonate. $^1$HNMR ($CDCl_3$, ppm): 4.6 (1H, s, O=C—(CHO—)—C=O); 4.3 (4H, q, O=C—O—$CH_2$—$CH_3$); 4.0–3.9 3.45–3.4 (4H, m system, —$CH_2$—O—$CH_2$—); 3.71 (1H, m, >C(—H)—O—); 2.0–1.85 1.8–1.65 (4H, m system, —$CH_2$—C(—O—)—$CH_2$—); 1.2 (6H, t, O=C—O—$CH_2$—$CH_3$, J 7 Hz).

Using in the procedure of example 2 a different alcohol (as reagent and solvent) or when, as described above, said alcohols and phenols cannot be used as solvents due to their poor volatility and high cost by reacting ethyl diazomalonate with 1.1 molar equivalents of said reagents in the presence of $[Rh(OAc)_2]_2$ in an inert solvent such as dichloromethane, ethyl acetate, dioxane, benzene, tetrahydrofuran and mixtures thereof in a reagents/solvents weight ratio of at least 2:1, the following compounds are obtained: ethyl phenoxymalonate;
ethyl p-chlorophenoxymalonate, chemically identical to a sample prepared according to C. A. 113: 211579 k;
ethyl 1-(3-ethoxy-propyl)-oxy-malonate;
ethyl 1-(4,7-dioxa-nonyl)-oxy-malonate;
ethyl 1-(3,6-dioxa-octyl)-oxy-malonate;
ethyl 1-(5-hydroxy-3-oxa-pentyl)-oxy-malonate;
ethyl cyclohexyloxymalonate;
ethyl cyclohexylmethoxymalonate;
ethyl 2-cyclohexyl-ethoxymalonate;
ethyl 3-cyclohexyl-propoxymalonate;
ethyl 2-cyclopentyl-ethoxymalonate;
ethyl 3-cyclopentyl-propoxymalonate;
ethyl 4-tetrahydropyranylmethoxy-malonate;
ethyl 4-tetrahydrothiapyranylmethoxy-malonate;
ethyl 2-(tetrahydropyran-4-yl)-ethoxy-malonate;
ethyl 3-(tetrahydropyran-4-yl)-propoxy-malonate;
ethyl 1,3-dioxan-5-yloxy-malonate;
ethyl 1-BOC-piperidin-4-yloxy-malonate;
ethyl 1-BOC-piperidin-4-yl-methoxy-malonate;
ethyl 1-isopropyl-piperidin-4-yl-methoxy-malonate;
ethyl 2-(1-isopropyl-piperazin-4-yl)ethoxy-malonate;
ethyl 2-(pyrrolidin-1-yl)ethoxy-malonate;
ethyl 2-(piperidin-1-yl)ethoxy-malonate;
ethyl benzyloxymalonate;
ethyl pyridin-4-yl-methoxymalonate;
ethyl pyridin-2-yl-methoxymalonate;
ethyl pyrimidin-2-yl-methoxymalonate;
ethyl triazin-2-yl-methoxymalonate;
ethyl pyridin-3-yl-methoxymalonate;
ethyl pyridin-3-yl-ethoxymalonate;
ethyl pyridin-4-yl-oxymalonate;
ethyl pyridin-3-yl-oxymalonate;
ethyl 4-(3,5-dimethyl-isoxazolyl)methoxymalonate;
ethyl 2-(2-thienyl)ethoxymalonate;
ethyl 2-phenylethoxy-malonate;
ethyl 2-(3,4,5-trimethoxy-phenyl)ethoxy-malonate;
ethyl 3-phenyl-propoxymalonate;
ethyl 3-(3,4,5-trimethoxy-phenyl)propoxymalonate;
ethyl (1S,2S)-10-pyranyloxy-malonate.

EXAMPLE 4

Using the methods described above by Kaloustian et al.; Juaristi et al.; Grossert et al.; Aveta et al., for the preparation of diethyl phenylthiomalonate, diethyl benzylthiomalonate, the following compounds are obtained: ethyl cyclohexylthiomalonate; ethyl 4-tetrahydropyranylthiomalonate; ethyl 3-pyridyl-methylthiomalonate; ethyl cyclohexylmethylthiomalonate; ethyl 2-cyclohexylethylthiomalonate; ethyl 4-tetrahydropyranyl-methylthiomalonate; ethyl 2-(2-ethoxyethyl)-thiomalonate; ethyl 1-(3-ethoxypropyl)-thiomalonate.

EXAMPLE 5

Under stirring and nitrogen atmosphere, 18.3 g of ethyl 2-(2-ethoxyethyl)oxy-malonate (74 mmoles) are added to a solution of sodium ethoxide in 35 ml of EtOH (prepared dissolving metal Na (1.95 g, 0.085 moles) in ethanol). Stirring is continued for 1 h at room temperature, then a solution of 3-BOC-amino-1-propylbromide (17.6 g, 74 mmoles) in EtOH (30 ml) is added dropwise. The reaction mixture is heated at 50° C. and kept overnight a this temperature. After 1h at 50° C. the formation of an abundant NaBr precipitate is observed. The progress of the reaction can be checked by TLC on $SiO_2$, eluent $CHCl_3$/MeOH 98:2. When the reaction is completed, the solvent is evaporated off under vacuum and the residue is partitioned between water and AcOEt. The aqueous phase is re-extracted with AcOEt (2×50 ml); the combined organic phases are washed to neutality with a 5% $NaH_2PO_4$ aqueous solution and water, and finally dried over sodium sulfate. After evaporation of the solvent and purification of the residue on a silica gel column, eluent $CHCl_3$/MeOH 98:1, 21 g (51.5 mmoles, 70% yield) of ethyl 5-BOC-amino-2-ethoxycarbonyl-2-[(2-ethoxy)-ethyloxy]-pentanoate are obtained.

$^1$HNMR ($CDCl_3$, ppm): 4.5 (1H, m, —NH—); 4.2 (4H, q, —$CO_2$—$CH_2$—, J 7 Hz); 3.7–3.6 (2H, m, —$CH_2$—O—CH<(C=O)$_2$—); 3.6–3.5 (2H, m, —O—$CH_2$—$CH_2$—O—); 3.4 (2H, q, $CH_3$—$CH_2$—O—, J 7 Hz); 3.1–3.0 (2H, m, —NH—$CH_2$—); 2.2–2.0 (2H, dd, —$CH_2$—$CH_2$—C(C=O—)$_2$—O—); 1.4 (9H, s, ($CH_3$)$_3$—C—O—CO—; 1.2 (6, t, —$CO_2$—$CH_2$—$CH_3$, J 7 Hz); 1.1 (3H, t, —O—$CH_2$—$CH_3$, J 7 Hz).

EXAMPLE 6

Using in the procedure described in example 5, one of the malonic esters described in examples 3 and 4, are obtained:

ethyl 5-BOC-amino-2-ethoxycarbonyl-2-[4-tetrahydropyranyloxy]-pentanoate; $^1$HNMR ($CDCl_3$, ppm): 4.55 (1H, m, —NH—); 4.22 (4H, q, —$CO_2$—$CH_2$—, J 7 Hz); 4.0–3.8 (1H, m, >C(—H)—O—); 4.0–3.8 3.25–3.0 (4H, m system, —$CH_2$—O—$CH_2$); 3.43 (2H, dt, —NH—$CH_2$—, J$_1$ 7 Hz); 2.02 (2H, dd, $_2$(O=C)>C(—O—)—$CH_2$ J$_1$ 10 Hz, J$_2$ 6 Hz); 2.0–1.45 (6H, —$CH_2$—CH(—O—)—$CH_2$—+—NH—$CH_2$—$CH_2$—$CH_2$—); 1.4 (9H, s, ($CH_3$)$_3$—C—O—CO—; 1.3 (6H, t, —$CO_2$—$CH_2$—$CH_3$, J 7 Hz).

ethyl 5-BOC-amino-2-ethoxycarbonyl-2-[4-tetrahydropyranyl-methoxy]-pentanoate;
ethyl 5-BOC-amino-2-ethoxycarbonyl-2-[4-tetrahydropyranyl-ethoxy]-pentanoate;
ethyl 5-BOC-amino-2-ethoxycarbonyl-2-[4-tetrahydropyranyl-propoxy]-pentanoate;
ethyl 5-BOC-amino-2-ethoxycarbonyl-2-[1,3-dioxan-5-yloxy]pentanoate;
ethyl 5-BOC-amino-2-ethoxycarbonyl-2-[1-BOC-piperidin-4-yloxy]-pentanoate;
ethyl 5-BOC-amino-2-ethoxycarbonyl-2-[1-BOC-piperidin-4-yl-methoxy]-pentanoate;
ethyl 5-BOC-amino-2-ethoxycarbonyl-2-[1-isopropyl-piperidin-4-yl-methoxy]-pentanoate;
ethyl 5-BOC-amino-2-ethoxycarbonyl-2-[2-(1-isopropylpiperazin-4-yl)ethoxy]-pentanoate;
ethyl 5-BOC-amino-2-ethoxycarbonyl-2-[2-(pyrrolidin-1-yl)-ethoxy]-pentanoate;
ethyl 5-BOC-amino-2-ethoxycarbonyl-2-[(piperidin-1-yl)ethoxy]pentanoate;
ethyl 5-BOC-amino-2-ethoxycarbonyl-2-[2-(cyclopentyl)-ethoxy]-pentanoate;
ethyl 5-BOC-amino-2-ethoxycarbonyl-2-[n-pentoxy]-pentanoate;
ethyl 5-BOC-amino-2-ethoxycarbonyl-2-benzyloxy-pentanoate;
ethyl 5-BOC-amino-2-ethoxycarbonyl-2-[pyridin-4-yl-methoxy]-pentanoate;
ethyl 5-BOC-amino-2-ethoxycarbonyl-2-[pyridin-2-yl-methoxy]-pentanoate;
ethyl 5-BOC-amino-2-ethoxycarbonyl-2-[pyridin-3-yl-methoxy]-pentanoate;
ethyl 5-BOC-amino-2-ethoxycarbonyl-2-[pyridin-3-yl-ethoxy]-pentanoate;
ethyl 5-BOC-amino-2-ethoxycarbonyl-2-[pyridin-4-yl-oxy]-pentanoate;
ethyl 5-BOC-amino-2-ethoxycarbonyl-2-[pyridin-3-yloxy]-pentanoate;
ethyl 5-BOC-amino-2-ethoxycarbonyl-2-[2-phenylthoxy]-pentanoate;
ethyl 5-BOC-amino-2-ethoxycarbonyl-2-[2-(3,4,5-trimethoxy-phenyl)-ethoxy]-pentanoate;
ethyl 5-BOC-amino-2-ethoxycarbonyl-2-[3-phenyl-propoxy]-pentanoate;
ethyl 5-BOC-amino-2-ethoxycarbonyl-2-[3,4,5-trimethoxy-phenyl-propoxy]-pentanoate;
ethyl 5-BOC-amino-2-ethoxycarbonyl-2-[(1S,2S)-10-pyranyloxy]-pentanoate;
ethyl 5-BOC-amino-2-ethoxycarbonyl-2-[cyclohexylthio]-pentanoate;
ethyl 5-BOC-amino-2-ethoxycarbonyl-2-[4-tetrahydropyranyl-thio]-pentanoate;
ethyl 5-BOC-amino-2-ethoxycarbonyl-2-[3-pyridylmethylthio]-pentanoate;
ethyl 5-BOC-amino-2-ethoxycarbonyl-2-[cyclohexylmethylthio]-pentanoate;
ethyl 5-BOC-amino-2-ethoxycarbonyl-2-[4-tetrahydropyranylmethylthio]-pentanoate;
ethyl 5-BOC-amino-2-ethoxycarbonyl-2-[2-(2-ethoxyethyl)-thio]-pentanoate;
ethyl 5-BOC-amino-2-ethoxycarbonyl-2-[1-(3-ethoxypropyl)thio]-pentanoate.

EXAMPLE 7

In the following, the general process for the hydrolysis of each of the esters of examples 5 and 6 is described: a solution of 50 mmoles of a diester, e.g. 5-BOC-amino-2-ethoxycarbonyl-2-[(2-ethoxy)ethyloxy]-pentanoate (20.2 g) in 25 ml of MeOH is added, under stirring, with 157 ml of a 0.63 N solution of $LiOH.H_2O$ in water/MeOH (1:1), equivalent to 100 mmoles of base. The mixture is stirred for 18 hours at room temperature to complete the reaction (TLC, $SiO_2$, eluent $BuOH/H_2O/AcOH$ 3:1:1), then methanol is evaporated off under vacuum. After freeze-drying, the solid residue is repeatedly suspended and triturated in AcOEt/$Et_2O$ to remove any traces of unreacted material, then is dissolved in water and filtered.

The aqueous solution is then freeze-dried to give 16.82 g of 5-BOC-amino-2-carboxy-2-[(2-ethoxy)ethyloxy]-pentanoic acid lithium salt, as a crystal powder.

$^1$HNMR ($D_2O$, ppm): 3.85 (2H, t, —$CH_2$—O—$CH_2$—$CH_2$—, J 5 Hz); 3.77 (2H, q, $CH_3$—$CH_2$—O—J 7 Hz); 3.6 (2H, t, —$CH_2$—O—$CH_2$—$CH_2$—, J 5 Hz); 2.12 (2H, m, —$CH_2$C(<$CO_2$—)$_2$—O—); 1.6 (9H, s, ($CH_3$)$_3$C—O—CO—NH); 1.6–1.5 (2H, m, —NH—$CH_2$—$CH_2$—$CH_2$—); 1.37 (3H, m, $CH_3$—$CH_2$—O—).

EXAMPLE 8

An aqueous solution of 5 g of 5-BOC-amino-2-carboxy-2-[4-tetrahydropyranyloxy]-pentanoic acid lithium salt [$^1$HNMR ($D_2O$, ppm): 4.2–4.05 3.7–3.5 (4H, m, —$CH_2$—O—$CH_2$—); 3.8 (OH, m, —$CH_2$—CH(—O—)—$CH_2$—); 3.23 (2H, t, —NH—$CH_2$—, J 6 Hz); 2.2–1.7 (6H, m syst., —$CH_2$—CH(—O)—$CH_2$—+—$CH_2$C(<$CO_2$)—O—); 1.6 (9H, s, ($CH_3$)$_3$C—O—CO—NH); 1.6–1.5 (2H, m, —NH—$CH_2$—$CH_2$—$CH_2$—)] is acidified to pH 4–5 by dilution under stirring with a 10% $KHSO_4$ aqueous solution. The separated acid is extracted repeatedly with ether ethyl and from the combined organic phases, washed with a 2% $KHSO_4$ aqueous solution and water to neutrality. By evaporation of the solvent under vacuum, 4.15 g of 5-BOC-amino-2-carboxy-2-[4-tetrahydropyranyloxy]-pentanoic acid are obtained. A solution of 3.5 g of the acid in EtOH is added with 2.93 g of 1-lysine in water to obtain 5.85 g of 5-BOC-amino-2-carboxy-2-[4-tetrahydropyranyloxy]-pentanoic acid 1-lysine salt. Analogously, by salification, the 5-BOC-amino-2-carboxy-2-[4-tetrahydropyranyloxy]-pentanoic acid tromethamine salt is obtained.

EXAMPLE 9

Using in the C-alkylation process of example 5, an ester selected from the group of ethyl 2-m-benzoylphenylmalonate, 6-methoxy-β-naphthylmalonate, phenylthioethylmalonate, 4-tetrahydrothiapyranylmethoxymalonate, 4-(3,5-dimethyl-isoxazolyl) methoxymalonate, 2-(2-thienyl)ethoxymalonate and cyclohexylpropylmalonate, the following compounds are obtained:

ethyl 5-BOC-amino-2-ethoxycarbonyl-2-[m-benzoylphenyl]-pentanoate;
ethyl 5-BOC-amino-2-ethoxycarbonyl-2-[6-methoxy-β-naphthyl]pentanoate;
ethyl 5-BOC-amino-2-ethoxycarbonyl-2-[4-(3,5-dimethylisoxazolyl)-methoxy]-pentanoate;
ethyl 5-BOC-amino-2-ethoxycarbonyl-2-[2-phenylthioethyl]-pentanoate;
ethyl 5-BOC-amino-2-ethoxycarbonyl-2-[2-(2-thienyl)-ethoxy]-pentanoate;
ethyl 5-BOC-amino-2-ethoxycarbonyl-2-[4-tetrahydrothiapyranylmethoxy]-pentanoate;
ethyl 5-BOC-amino-2-ethoxycarbonyl-2-[3-cyclohexylprolyl]-pentanoate:

$^1$HNMR (CDCl$_3$, ppm): 4.53 (1H, bs NH); 4.18 (4H, q. —CO$_2$—CH$_2$—CH$_3$, J 7 Hz); 3.11 (2H, m, NH—CH$_2$—); 1.9–1.85 (4H, m, —CH$_2$—C(<(CO$_2$)$_2$)—CH$_2$—); 1.7–1.6 1.5–1.3–1.3–1.1 (17 H complex system of m —NH—CH$_2$—CH$_2$—+

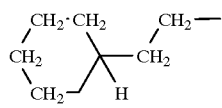

1.45 (9H, s. (CH$_3$)$_3$—OCONH); 1.25 (6H, t, —CO$_2$—CH$_2$—CH$_3$; J 7 Hz).

EXAMPLE 10

Using in the process of example 5 ethyl 3-cyclohexyl-2-ethoxycarbonyl-propionate and a suitable halide, selected from the group of α-, β- and γ-pyridomethyl chloride or bromide, 2-BOC-aminoethyl bromide, 2-BOC-ethylaminoethyl bromide, 3-BOC-aminopropyl bromide, 3-BOC-isopropylaminopropyl bromide, (2S) (1-BOC-pyrrolidin-2-yl)-methyl bromide, (pyrrolidin-1-yl)-ethyl bromide and furfuryl bromide, the following compounds are obtained:

ethyl 3-(2-pyridyl)-2-cyclohexylmethyl-2-ethoxycarbonyl-propanoate;
ethyl 3-(3-pyridyl)-2-cyclohexylmethyl-2-ethoxycarbonyl-propanoate;
ethyl 3-(4-pyridyl)-2-cyclohexylmethyl-2-ethoxycarbonyl-propanoate;
ethyl 4-BOC-amino-2-(cyclohexylmethyl)-2-ethoxycarbonyl-butanoate;
ethyl 4-BOC-ethylamino-2-(cyclohexylmethyl)-2-ethoxycarbonyl-butanoate;
ethyl 5-BOC-isopropylamino-2-(cyclohexylmethyl)-2-ethoxycarbonyl-pentanoate;
ethyl 3-[(S) N-BOC-pyrrolidin-2'-yl]-2-cyclohexylmethyl-2-ethoxycarbonyl-propanoate;
ethyl 4-(pyrrolidin-1'-yl)-2-ethoxycarbonyl-butanoate;
ethyl 5-BOC-amino-2-(cyclohexylmethyl)-2-ethoxycarbonyl-pentanoate;
ethyl 3-(fur-2-yl)-2-cyclohexylmethyl-2-ethoxycarbonyl-propanoate, which by reaction with formaldehyde and dimethylamine hydrochloride yields ethyl 3-(5-dimethylaminomethyl-fur-2-yl)-2-cyclohexylmethyl-2-ethoxycarbonyl-propanoate.

EXAMPLE 11

A solution of ethyl 5-BOC-amino-2-ethoxycarbonyl-2-[4-tetrahydropyranyloxy]-pentanoate in CH$_2$Cl$_2$ (20 ml), cooled at 0–5° C., is added with trifluoroacetic acid (5 ml). After a night at room temperature, the mixture is evaporated under vacuum to obtain, after trituration of the residue in ethyl ether, 3.86 g of 4,4-diethoxycarbonyl-4-(4-tetrahydropyranyloxy)-butylammonium trifluoroacetate. A suspension of the salt in AcOEt (25 ml) is neutralized, under stirring at 0–5° C., by careful addition of a 5% sodium bicarbonate aqueous solution. After separating the organic phase and re-extracting the aqueous phase with AcOEt (3×5 ml), the combined organic phases are dried over Na$_2$SO$_4$, and solvent is evaporated off to obtain 2.73 g of ethyl 5-amino-2-ethoxycarbonyl-2-[4-tetrahydropyranyloxy]-pentanoate.

The cleavage of the tert-butoxycarbonyl-protecting group is carried out analogously, and each of the BOC-derivatives of examples 5, 6, 9 and 10 is converted into the corresponding amine. Thus, for instance, by reacting with a molar excess of trifluoroacetic acid in CH$_2$Cl$_2$ the BOC derivatives:

ethyl 5-BOC-amino-2-ethoxycarbonyl-2-[1-BOC-piperidin-4-yloxy]-pentanoate; ethyl 5-BOC-amino-2-ethoxycarbonyl-2-[1-BOC-piperidin-4-yl-methoxy]-pentanoate; ethyl 4-BOC-amino-2-(cyclohexylmethyl)-2-ethoxycarbonyl-butanoate;
ethyl 4-BOC-ethylamino-2-(cyclohexylmethyl)-2-ethoxycarbonyl-butanoate; ethyl 5-BOC-isopropylamino-2-(cyclohexylmethyl)-2-ethoxycarbonylpentanoate; ethyl 5-BOC-amino-2-(cyclohexylmethyl)-2-ethoxycarbonyl-pentanoate, the corresponding amines are obtained:
ethyl 5-amino-2-ethoxycarbonyl-2-[piperidin-4-yloxy]-pentanoate;
ethyl 5-amino-2-ethoxycarbonyl-2-[piperidin-4-yl-methoxy]-pentanoate;
ethyl 4-amino-2-(cyclohexylmethyl)-2-ethoxycarbonyl-butanoate;
ethyl 4-ethylamino-2-(cyclohexylmethyl)-2-ethoxycarbonyl-butanoate;
ethyl 5-isopropylamino-2-(cyclohexylmethyl)-2-ethoxycarbonyl-pentanoate;
ethyl 5-amino-2-(cyclohexylmethyl)-2-ethoxycarbonyl-pentanoate.

EXAMPLE 12

According to the general method described by C. A. Maryanoff et al., J. Org. Chem., 51, 1882, 1986, 0.005 mmoles (0.062 g) of aminoiminomethanesulfonic acid are added at room temperature to a solution of 0.0065 mmoles (2.06 g) of ethyl 5-amino-2-ethoxycarbonyl-2-[4-tetrahydropyranyloxy]-pentanoate in acetonitrile (5 ml) to separate 3.7 g of N-(4,4-diethoxycarbonyl-4-tetrahydropyranyloxy)-butyl guanidinium sulfate.

Analogously, but using methylaminoiminomethanesulfonic and anilinoimino-methanesulfonic acids, the following compounds are obtained: N-methyl-N'-(4,4-diethoxycarbonyl-4-tetrahydropyranyl-oxy)-butyl guanidinium sulfate N-phenyl-N'-(4,4-diethoxycarbonyl-4-tetrahydropyranyl-oxy)-butyl guanidinium sulfate.

By reaction with 1-methylthio-1-methylamino-2-nitroethene, 1,1-ethenediamine,N-(4,4-diethoxycarbonyl-4-tetrahydropyranyloxy)-butyl),N'-methyl-2-nitro is obtained.

EXAMPLE 13

A solution of ethyl 5-amino-2-ethoxycarbonyl-2-[cyclohexylmethylthio]-pentanoate (3.63 g, 1.05 mmoles) and dimethyl N-cyanoimidodithiocarbonate (2 g, 1.37 mmoles) in isopropanol (15 ml) is kept at room temperature for 4h; then is diluted with 30 ml of $Et_2O$ and the mixture is kept at room temperature overnight. 4.01 g of N-[4,4-diethoxycarbonyl-4-cyclohexylmethyltiobutyl]-N'-cyano-S-methyl-isothiourea separate.

A solution of 2 g of the compound with a 5% ethylamine solution in EtOH is refluxed to yield 1.9 g of N-[4,4-diethoxycarbonyl-4-cyclohexylmethylthiobutyl]-N'-ethyl-cyanoguanidine.

Analogously, by reaction with (R,S)-3,3-dimethyl-2-butylamine, (R,S) N-[4,4-diethoxycarbonyl-4-cyclohexylmethylthio-butyl]-N'-3,3-dimethyl-2-butyl-cyanoguanidine is obtained.

EXAMPLE 14

6 g of ethyl 2-(2-ethoxyethyl)oxymalonate (24.65 mmoles) are added to a solution of sodium ethoxide in EtOH (15 ml, prepared by dissolution of 0.65 g, 0.028 moles metal Na) under stirring and nitrogen atmosphere. Stirring is continued for 1 h at room temperature, then a solution of 3-trityloxy-1-propyl-bromide (9.4 g, 24.7 mmoles) in EtOH (20 ml) is added dropwise. The reaction mixture is heated at 50° C. and kept at this temperature overnight. When the reaction is completed, the solvent is evaporated off under vacuum and the residue is partitioned between water and AcOEt. The aqueous phase is re-extracted with AcOEt (2×50 ml), the combined organic phases are washed to neutrality with a 5% $NaH_2PO_4$ aqueous solution, then with water, and finally dried over sodium sulfate. After evaporation of solvent, the resulting solution of crude ethyl 5-trityloxy-2-ethoxycarbonyl-2-[(2-ethoxy)ethyloxy]-pentanoate in EtOH is treated with 0.3 g of p-toluenesulfonic.$H_2O$ acid and kept for 12 h at room temperature. After evaporation of solvent, the residue is dissolved in dichloromethane (15 ml) and the organic phase is washed with 2×5 of 5% aqueous $NaHCO_3$, then with water to neutrality, dried over $Na_2SO_4$, the solvent is evaporated off and the residue is purified on a silica gel column (eluent $CHCl_3$/MeOH 98:1.5), to obtain 6.42 g of ethyl 5-hydroxy-2-[(2-ethoxy)ethyloxy]-2-ethoxycarbonyl-pentanoate.

A solution of 1.77 g of the compound in 4 ml of pyridine is reacted with 2.5 g of p-toluenesulfonyl chloride to give 2.3 g of ethyl 5-p-toluenesulfonyloxy-2-[(2-ethoxy)ethyloxy]-2-ethoxycarbonyl-pentanoate, which by reaction with LiBr in acetone, yields:
ethyl 5-bromo-2-[(2-ethoxy)ethyloxyl]-2-ethoxycarbonyl-pentanoate.

A solution of 1 g of ethyl 5-bromo-2-[(2-ethoxy)ethyloxy]-2-ethoxycarbonyl-pentanoate in 5 ml of EtOH, added with 0.8 g of thiourea, is refluxed for 4 hours, then cooled to separate a crystalline precipitate of S-(4,4-diethoxycarbonyl-4-(2(2-ethoxy)-ethoxy)butyl isothiouronium bromide.

EXAMPLE 15

Using, in the process of example 14, ethyl 2-(1-isopropylpiperidin-4-ylmethoxy)-malonate, the following compounds are obtained:
ethyl 5-hydroxy-2-[2-(1-isopropylpiperidin-4-ylmethoxy)]-2-ethoxycarbonyl-pentanoate;
ethyl 5-bromo-2-[2-(1-isopropylpiperidin-4-ylmethoxy)]-2-ethoxycarbonyl-pentanoate;
S-(4,4-diethoxycarbonyl-4-[2-(1-isopropylpiperidin-4-ylmethoxy)]-butyl isothiouronium bromide,
and by reaction with N-butylthiourea, S-(4,4-diethoxycarbonyl-4-[2-(1-isopropylpiperidin-4-ylmethoxy)]-butyl,N-butyl isothiouronium bromide.

EXAMPLE 16

A solution of 0.1 g of potassium tert-butylate in 6 ml of THF/EtOH 1:2 is added, under nitrogen atmosphere, with 0.1 g of 2-imidazolidinethione and 0.41 g of ethyl 5-bromo-2-[2-(1-isopropylpiperidin-4-ylmethoxy)]-2-ethoxycarbonyl-pentanoate. The mixture is refluxed for 2h, the solvent is evaporated off and the residue is partitioned between AcOEt and water. After the usual work up, the solvent is evaporated off and the residue is purified on a silica gel column, to obtain 0.32 g of ethyl 5-(4,5-dihydro-imidazol-2-yl-2-thio)-2-[2-(1-isopropylpiperidin-4-ylmethoxy)]-pentanoate.

Using as mercaptans: β-pyridyl-methyl-mercaptan and 3,4,5,6-tetrahydro-2-pyrimidinothiol, the following compounds are also obtained:
ethyl 5-(β-pyridyl-methylthio)-2-[2-(1-isopropylpiperidin-4-ylmethoxy)]-2-ethoxycarbonyl-pentanoate;
ethyl 5-(3,4,5,5-tetrahydro-pyrimidin-2-yl-thio)-2-[2-(1-isopropylpiperidin-4-ylmethoxy)]-2-ethoxycarbonyl-pentanoate;
ethyl 5-(4,5-dihydro-imidazol-2-yl-2-thio)-2-[(2-ethoxy)ethyloxy]-2-ethoxycarbonyl-pentanoate;
ethyl 5-(β-pyridyl-methylthio)-2-[(2-ethoxy)ethyloxy]-2-ethoxycarbonyl-pentanoate;
ethyl 5-(3,4,5,5-tetrahydro-pyrimidin-2-yl-thio)-2-[(2-ethoxy)ethyloxy]-2-ethoxycarbonyl-pentanoate.

EXAMPLE 17

Using, in the process of example 14, ethyl 3-cyclohexyl-2-ethoxycarbonyl-propionate and 2-trityloxyethyl bromide, 4-cyclohexyl-2,2-diethoxycarbonyl-butan-1-ol is obtained and then by reaction in dichloromethane with triphenylphosphine and tetrabromomethane, 4-cyclohexyl-2,2-diethoxy-1-butyl-bromide. A solution of 0.1 g of potassium tert-butylate in 6 ml of THF/EtOH 1:2 is added with 0.15 g of furfurylmercaptan and 0.38 g of 4-cyclohexyl-2,2-diethoxy-1-butyl bromide. The mixture is refluxed for 4 hours under nitrogen atmosphere, evaporated and partitioned between AcOEt and water. After the usual work up, the solvent is evaporated off and the residue is purified on a silica gel column, to obtain 0.34 g of ethyl 4-(fur-2-ylmethylthio)-2-ethoxycarbonyl-2-cyclohexylmethyl-butanoate.

A solution of 0.2 g of the compound in EtOH (6 ml), dimethylamine hydrochloride (0.06 g) and paraformaldehyde (0.045 g) is refluxed for 4 hours, the major part of the solvent is evaporated off, the residue is diluted with water (10 mi) and extracted with AcOEt. The organic phases are washed with 1×3 ml of water and then discarded. The aqueous phases are combined, alkalinized with potassium bicarbonate and re-extracted with AcOEt. The organic phases are combined to give, after the usual work up and purification of the residue on a silica gel column, 0.18 g of 4-(5-dimethylaminomethyl-fur-2-ylmethylthio)-2-ethoxycarbonyl-2-cyclohexylmethyl-butanoate.

EXAMPLE 18

Using, in the process of example 1, diallyl malonate, by reaction of the resulting allyl diazomalonate with morpholinylethanol and thiamorpholinylethanol, the following compounds are obtained:
allyl morpholinylethoxymalonate and allyl thiamorpholinylethoxymalonate, which are reacted according to the process of example 5 respectively with 2-benzyloxycarbonylaminoethyl bromide, 4-benzyloxycarbonylaminobutyl bromide, (S) 2-BOC-amino-propyl bromide and (S) 3-phenyl-2-BOC-amino-propyl bromide to obtain:
allyl 4-benzyloxycarbonylamino-2-(allyloxycarbonyl)-2-(morpholinyl-4-ethoxy)-butanoate;
allyl 4-benzyloxycarbonylamino-2-(allyloxycarbonyl)-2-(morpholinyl-4-ethoxy)-hexanoate;
allyl (S) 4-tert-butoxycarbonylamino-2-(allyloxycarbonyl)-2-(thiamorpholinyl-4-ethoxy)-pentanoate;
allyl (S) 5-phenyl-4-tert-butoxycarbonylamino-2-(allyloxycarbonyl)-2-(morpholinyl-4-ethoxy)-pentanoate and after cleavage of the Z and BOC protecting groups, the following compounds are obtained:
allyl 4-amino-2-(allyloxycarbonyl)-2-(morpholinyl-4-ethoxy)-butanoate;
allyl 4-amino-2-(allyloxycarbonyl)-2-(morpholinyl-4-ethoxy)-hexanoate;
allyl (S) 4-amino-2-(allyloxycarbonyl)-2-(thiamorpholinyl-4-ethoxy)-pentanoate;
allyl (S) 5-phenyl-4-amino-2-(allyloxycarbonyl)-2-(morpholinyl-4-ethoxy)-pentanoate.

EXAMPLE 19

Using, in the process of Example 9, allyl cyclohexylpropylmalonate, the following compound is obtained:
allyl 5-BOC-amino-2-allyloxycarbonyl-2-[3-cyclohexyl-propyl]-pentanoate: $^1$HNMR (CDCl$_3$, ppm): 4.53 (1H, bs NH); 3.11 (2H, m, NH—CH$_2$—); 1.9–1.85 (4H, m, —CH$_2$—C(<(CO$_2$)$_2$)—CH$_2$—); 1.7–1.6 1.5–1.3-1.3–1.1 (17 H complex system of m —NH—CH$_2$—CH$_2$—+

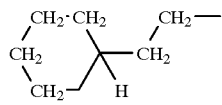

1.45 (9H, s, (CH$_3$)$_3$—OCONH); 1.25 (6H, t, —CO$_2$—CH$_2$—CH$_3$; J 7 Hz) which is converted into potassium 5-BOC-amino-2-carboxy-2-[3-cyclohexylpropyl]-pentanoate with potassium hexanoate and triphenylphosphine.

We claim:

1. A compound of the formula

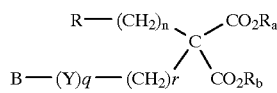

wherein n is zero or an integer 1 to 6, q is zero or the integer 1, and r is zero or the integer 1 to 3;
R$_a$ and R$_b$ are independently hydrogen, an alkali or alkaline-earth metal cation, an ammonium or C$_1$–C$_{10}$ alkylammonium cation, C$_1$–C$_4$ alkyl, C$_1$–C$_{10}$ alkoxyethyl, allyl, p-methoxybenzyl, and amino-C$_2$–C$_4$ alkyl;
Y is CH$_2$,O, or S;
B is 2-propyl, —(CH$_2$)$_2$—(OCH$_2$CH$_2$)$_t$H, —(CH$_2$)$_2$—(OCH$_2$CH$_2$)$_t$OH, wherein t is an integer 1 to 3, or a group of the formula:

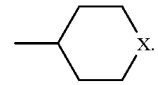

in which X is a single bond between 2 carbon atoms, CH$_2$, O, or S;
R is a group of the formula

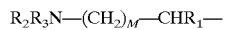

wherein M is zero or an integer 1 to 3 and
when R$_1$ is hydrogen and R$_2$ is hydrogen, C$_1$–C$_7$-alkyl, C$_3$–C$_7$ cycloalkyl or benzyl, then R$_3$ is hydrogen, C$_1$–C$_4$-alkyl, tert-butoxycarbonyl, 9-fluorenylmethoxycarbonyl, benzyloxycarbonyl, p-methoxybenzyloxycarbonyl, or one of the groups of formula R$_d$N=C(YR$_e$)—, R$_d$NH—C(=NH)—, R$_d$NH—C(=N—CN)—, or CH$_3$NH—C(=CH—NO$_2$)—wherein R$_d$ and R$_e$ are independently hydrogen, C$_1$–C$_4$—alkyl, C$_3$–C$_7$ cycloalkyl, or benzyl, and Y is O or S;
when R$_1$ is hydrogen, then R$_2$ and R$_3$, taken together with the nitrogen atom which they are linked to, can form a 5- or 6- membered nitrogen heterocyclic ring of formula:

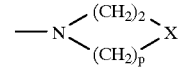

wherein p is the integer 2 or 3 and X is a single bond between 2 carbon atoms, CH$_2$, O, or S;
the optically active forms of the enantiomers, diastereomers, and the mixtures thereof, and the pharmaceutically acceptable salts thereof.

2. The compound of claim 1, wherein R$_a$ and R$_b$ are both C$_1$–C$_4$ alkyl, hydrogen, or an alkali or alkaline-earth metal cation.

3. The compound of claim 1, wherein B-(Y)$_q$—(CH$_2$)$_r$— is selected from cyclohexylmethyl, 3-cyclohexylpropyl, 4-tetrahydropyranyloxy, 2-ethoxyethyloxy, and cyclohexylthio.

4. A pharmaceutical composition containing as the active ingredient a compound of claim 1 in admixture with a suitable carrier.

5. A method of treating bone dysmetabolism in an animal in need of such treatment, comprising administering to the animal a bone dysmetabolism treatment effective amount of a compound of claim 1.

6. The method of claim 5, wherein the treatment comprises administering to the animal a dosage of 2 to 1200 mg of said compound.

7. The method of claim 6, wherein the dosage is administered daily.

* * * * *